(12) United States Patent
Drummond et al.

(10) Patent No.: US 7,022,673 B2
(45) Date of Patent: *Apr. 4, 2006

(54) METHOD FOR INCREASING THE SERUM HALF-LIFE OF A BIOLOGICALLY ACTIVE MOLECULE

(75) Inventors: Robert J. Drummond, Richmond, CA (US); Steve Rosenberg, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 10/123,092

(22) Filed: Apr. 11, 2002

(65) Prior Publication Data

US 2002/0182705 A1 Dec. 5, 2002

Related U.S. Application Data

(63) Continuation of application No. 09/263,117, filed on Mar. 5, 1999, now Pat. No. 6,423,685.
(60) Provisional application No. 60/076,964, filed on Mar. 5, 1998.

(51) Int. Cl.
*A61K 38/00* (2006.01)
*A61K 39/385* (2006.01)
*C07K 1/00* (2006.01)
*C12N 9/72* (2006.01)

(52) U.S. Cl. .............................. 514/12; 514/2; 530/324; 530/345; 530/402; 530/405; 530/409; 530/410; 530/421; 435/69.2; 435/180; 435/181; 435/215; 424/193.1

(58) Field of Classification Search .................. 514/12, 514/2; 530/324, 345, 402, 405, 409, 410, 530/421; 435/69.2, 180, 181, 215; 424/193.1
See application file for complete search history.

(56) References Cited

U.S. PATENT DOCUMENTS

| 4,179,337 | A | * | 12/1979 | Davis et al. ................. 435/181 |
| 5,089,261 | A |   | 2/1992  | Nitecki et al. |
| 5,281,698 | A | * | 1/1994  | Nitecki ........................ 530/351 |
| 5,362,852 | A | * | 11/1994 | Geoghegan ................. 530/345 |
| 6,423,685 | B1 | * | 7/2002 | Drummond et al. .......... 514/12 |

FOREIGN PATENT DOCUMENTS

| EP | 442724 A2 | 8/1991 |
| EP | 539167 A2 | 4/1993 |
| WO | WO90/07938 | 7/1990 |
| WO | WO91/19735 | 12/1991 |
| WO | WO94/06151 | 3/1994 |
| WO | WO94/13322 | 6/1994 |
| WO | WO 94/28145 | * 12/1994 |
| WO | WO95/06058 | 3/1995 |

OTHER PUBLICATIONS

Delgado et al., Critical Reviews in Therapeutic Drug Carrier Systems, vol. 9, No. 3,4, pp. 249–304, 1992.*
Abuchowski et al. (1977), "Effect of Covalent Attachment of Polyethylene Glycol on Immujogenicity and Circulating Life of Rovine Liver Catalaso," *The Journal of Biological Chemistry* 252(11):3582–3586.
Abuchowski et al. (1984), "Cancer Therapy with Chemically Modified Enzymes. I. Antitumor Properties of Polyethylene Glycol–Asparaginaso Conjugates," *Cancer Biochem Biophys.* 7:175–186.
Beauchamp et al. (1983), "A New Procedure for the Synthesis of Polyethylene Glycol–Protein Adducts; Effects on Function, Receptor Recognition, and Clearance of Superoxide Dismutase, Lactoferrin, and $\alpha_2$–Macroglubulin," *Analytical Biochemistry* 131:25–33.
Fields et al. (1968), "A Spectrophotometric Method for the Microdetermination of Periodate," *Biochem. J.* 108:883–887.
Gaertner et al. (1992), "Construction of Protein Analogues by Site–Specific Condensation of Unprotected Fragments," *Bioconjugate Chem.* 3:262–268.
Gaertner et al. (1994), "Chemo–Enzymatic Backbone Engineering of Proteins,"0 *The Journal of Biological Chemistry* 269(10): 7224–7230.
Gaertner et al. (1996), "Site–Specific Attachment of Functionalized Polyethylene glycol) to the Amino Terminus of Proteins." Bioconjugate Chem. 7:38–44.
Geoghengan et al. (1992), "Site–Directed Conjugation of Nonpeptide Groups and Proteins vic periodate Oxidation of a 2–Amino Alcohol. Application to Modification at N–Terminal Serine," *Bioconjugate Chem.* 3:183–146.
Goodson et al., (1994), "Hight–Affinity Urokinase Receptor Antagonists Identified with Bacteriophage Peptide Display," *Proc. Natl. Acad. Sci. USA* 91:7129–7133.
Veronese et al. (1985), "Surface Modification of Proteins, Activation of Monomethoxy–Polyethylene Glycols by Phenlychlorformates and Modification of Ribonuclease and Superoxide Dismutase," *Applied Biochemistry and Biotechnology* 11: 141–152.

* cited by examiner

*Primary Examiner*—Jon Weber
*Assistant Examiner*—Abdel A. Mohamed
(74) *Attorney, Agent, or Firm*—Carol A. Schneider; Young J. Suh; Alisa A. Harbin

(57) ABSTRACT

A method is provided for preparing a biologically active molecule having an increased serum half-life. The method involves conjugating a polymer such as polyethylene glycol to the biologically active molecule. Also provided are polypeptide drugs having an increased serum half-life, e.g., human urokinase plasminogen activator (human "uPA" or "hUPA") or a fragment or derivative thereof. Pharmaceutical compositions containing such molecules and methods of using them to treat uPA-mediated and uPA receptor-mediated disorders are also provided.

16 Claims, 4 Drawing Sheets

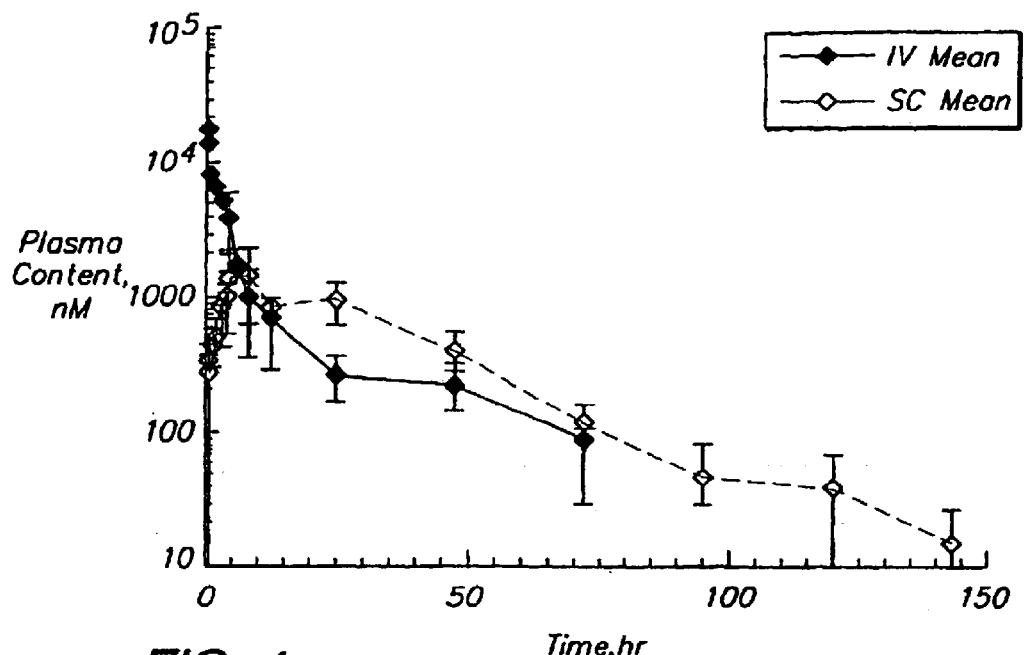
FIG. 1
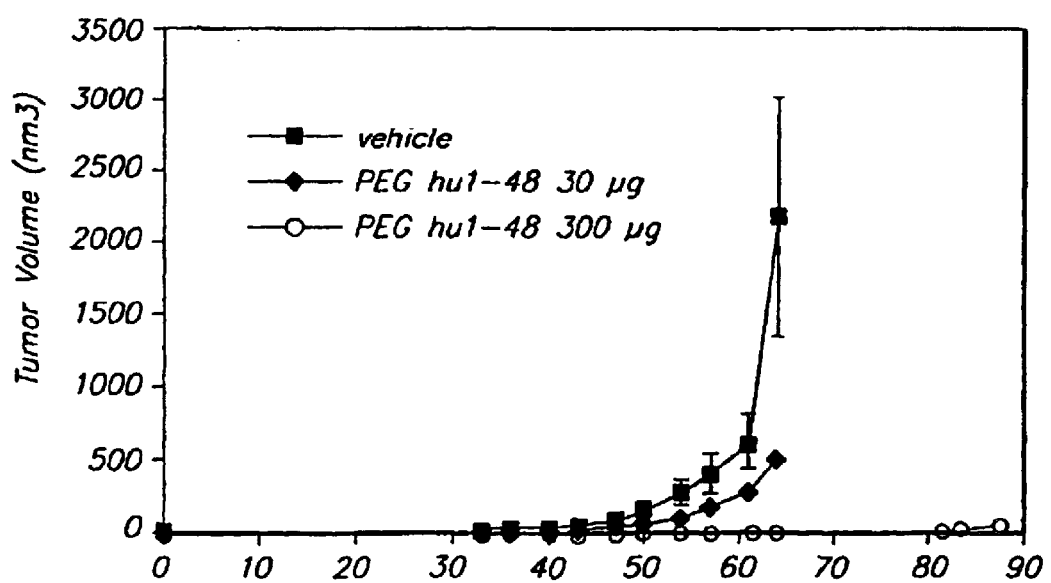
FIG. 2 Day Post Tumor Implantation

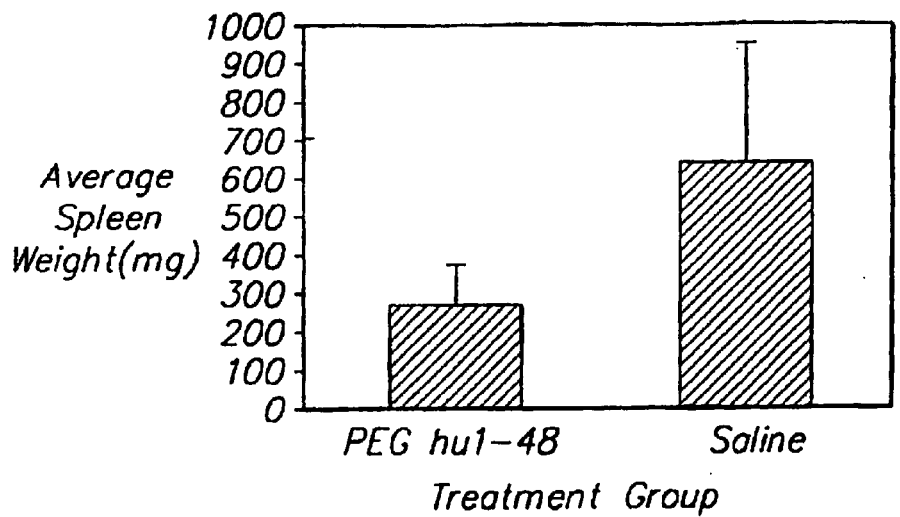
FIG. 4A
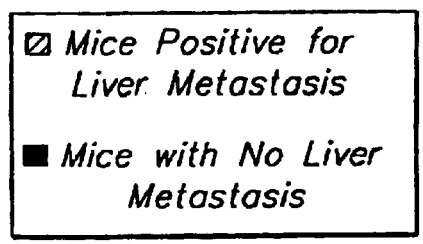
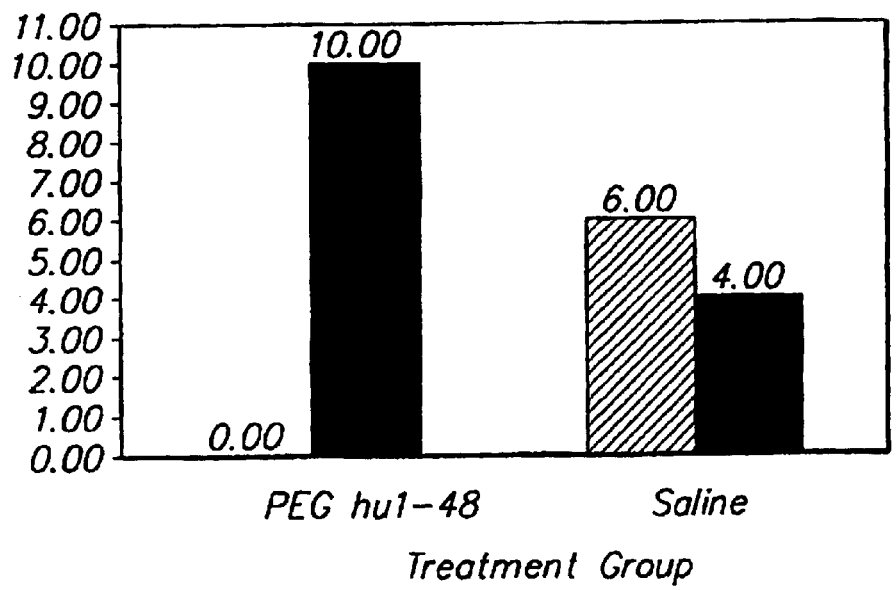
FIG. 4B

US 7,022,673 B2

METHOD FOR INCREASING THE SERUM HALF-LIFE OF A BIOLOGICALLY ACTIVE MOLECULE

CROSS-REFERENCE TO RELATED APPLICATIONS

This application is a continuation of U.S. Ser. No. 09/263,117 filed on Mar. 5, 1999 and now issued as U.S. Pat. No. 6,423,685, which claims priority to U.S. Ser. No. 60/076,964, a provisional patent application filed on Mar. 5, 1998.

TECHNICAL FIELD

This invention relates generally to the chemical modification of biologically active molecules, and more particularly relates to a method for modifying biologically active molecules to increase their serum half-life.

BACKGROUND

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

A possible solution to an undesirably short serum half-life of a pharmaceutical agent is to covalently attach to the agent molecules which may increase the half-life. Previously, it has been shown that attachment of polymers to polypeptides may increase their serum half-lives. See, for example, European Patent Publication No. 0 442 724 A2, which describes "PEGylated" interleukin-6 derivatives (i.e., interleukin derivatives bound to polyethylene glycol, or "PEG") having an extended serum half-life. Attachment of drugs to polymers has also been reported to increase their water solubility, stability during storage and reduce their immunogenicity (published patent applications EP 0 539 167 A2, WO 94/13322). Conjugates of IL-2 or muteins thereof with polymers have also been reported to have reduced immunogenicity, increased solubility and increased half-lives (U.S. Pat. Nos. 5,362,852, 5,089,261, 5,281,698 and published patent application WO 90/07938).

However, the attachment of polymers can lead to decreases in drug activity. Incomplete or nonuniform attachment leads to a mixed population of compounds having differing properties. Additionally, the changes in half-lives resulting from such modifications are unpredictable. For example, conjugation of different polyethylene glycols to IL-8, G-CSF and IL-1ra produced molecules having a variety of activities and half-lives (Gaertner and Offord, (1996), *Bioconjugate Chem.* 7:38–44). Conjugation of IL-8 to PEG$_{20}$ $_{kD}$ produced no change in its half-life, while conjugation of PEG$_{20}$ $_{kD}$ to IL-1ra gave an almost seven-fold increase in half-life. Additionally, the IL-8/PEG$_{20}$ $_{kD}$ conjugate was ten- to twenty-fold less effective than the native protein.

Accordingly, a method which is capable of increasing the serum half-life of a biologically active molecule, without seriously diminishing the biological function of the molecule, would be highly desirable.

BRIEF DESCRIPTION OF THE FIGURES

FIG. 1 is a graph illustrating the plasma disposition of PEG hu1-48 in Cynomologous Monkeys after intravenous (IV) and subcutaneous (SC) (10 mg/kg) dosing, as evaluated in Example 4.

FIG. 2 is a graph showing the effect of 300 μg hu1-48SR, 30 μg PEG hu1-48, and vehicle on the size of the tumor in mice infected with human breast carcinoma MDA MB231 cell lines, as evaluated in Example 6.

FIGS. 4A and 4B are graphs showing the average splenic weight and incidence of metastases, respectively, of nude mice injected intrasplenically with human colorectal carcinoma cancer KM12 L4A cells followed by treatment with PEG hu1-48, as described in Example 8.

SUMMARY OF THE INVENTION

Figure 3:
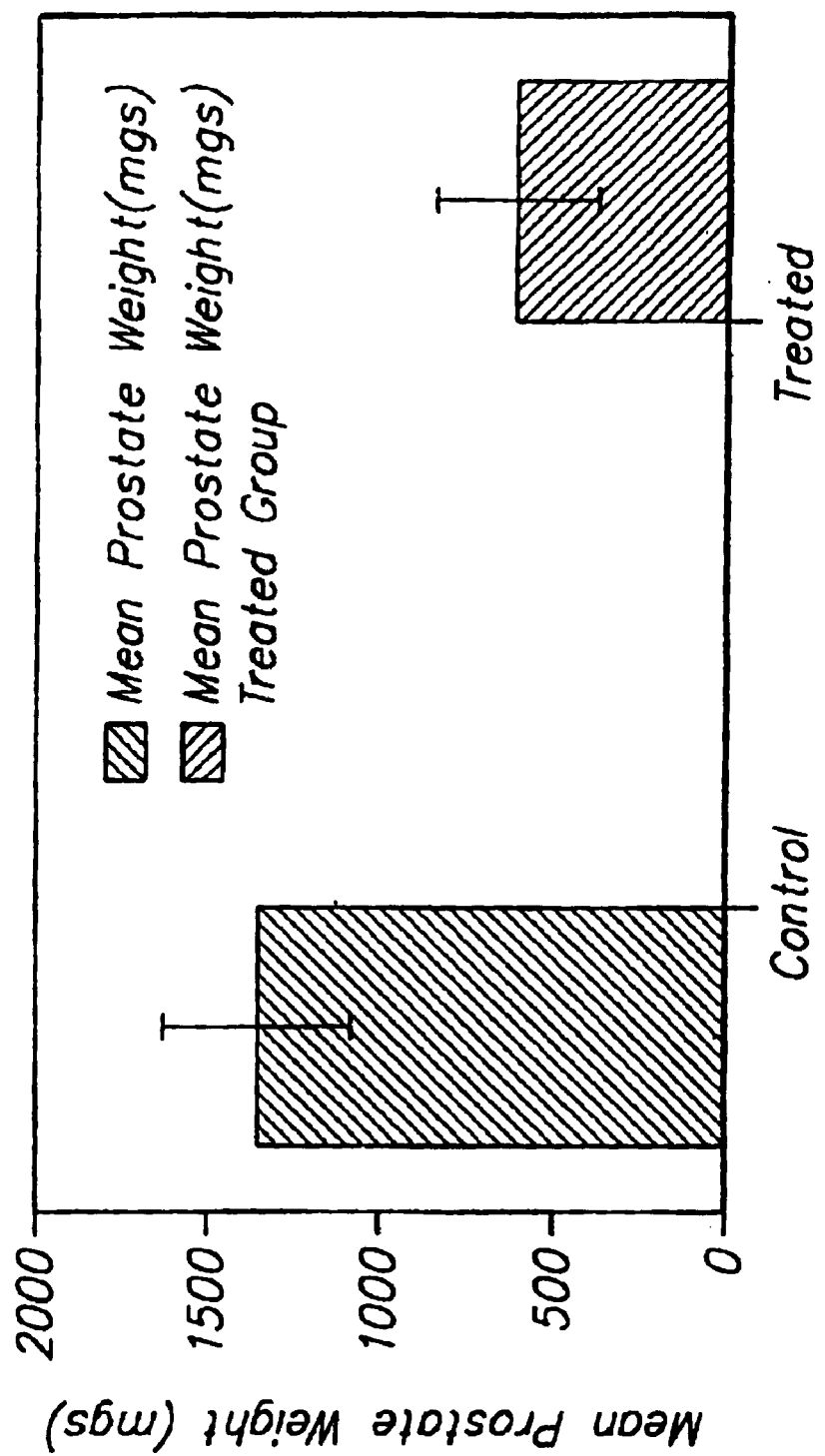
FIG. 3 is a graph showing reduction in tumor growth following treatment with 300 μg PEG hu1-48 as measured by the mean prostate weight of mice injected with human prostate carcinoma PC3-mm2 cells, as evaluated in Example 7.

Thus there is a need in the art for a method for modifying a biologically active molecule without abolishing its biological activity. There is a further need in the art to provide a method for increasing the serum half-life of such a molecule. There is yet a further need for a method of increasing the serum half-life of a biologically active molecule which produces a single species of product having uniform biological and pharmacokinetic properties.

Accordingly, it is a primary object of the invention to address the above-described needs by providing a method for increasing the serum half-life of a biologically active molecule.

It is another object of the invention to provide such a method which avoids modification of sites necessary for biological activity present within the molecule.

It is still another object of the invention to provide such a method wherein the molecule is a polypeptide.

It is an additional object of the invention to provide such a method wherein the polypeptide is "PEGylated," i.e., coupled to PEG, for example by reaction of a PEG hydrazide with an aldehyde moiety present at the N-terminus of the polypeptide.

It is yet another object of the invention to provide such a method wherein the serum half-life of the polypeptide is increased by site-specific attachment of a polymer such as polyethylene glycol to the N-terminus of the polypeptide chain.

It is a further object of the invention to provide a modified molecule having a longer serum half-life than the native molecule.

It is still another object of the invention to provide a pharmaceutical composition comprising a conjugate of a polymer and a biologically active molecule in combination with a pharmaceutically acceptable carrier or excipient.

It is yet a further object of the invention to provide a method of treating a urokinase plasminogen activator- ("uPA-") mediated disorder by administering a pharmaceutically acceptable composition comprising a conjugate of uPA$_{1-48}$ and a polymer.

Additional objects, advantages and novel features of the invention will be set forth in part in the description which follows, and in part will become apparent to those skilled in the art upon examination of the following, or may be learned by practice of the invention.

In one embodiment, the present invention relates to a method for chemically modifying a molecule to increase the serum half-life thereof, preferably in a site-specific manner without modification of any sites necessary for biological activity, such as receptor binding or enzymatic activity. The molecule is preferably, although not necessarily, a polypeptide. The method involves binding the molecule to a polymer such as polyethylene glycol, e.g. by reacting a hydrazide-activated form of polyethylene glycol (referred to herein as "polyethylene glycol hydrazide" or "PEG hydrazide") with an aldehyde moiety present on the molecule. When the molecule to be modified is a polypeptide, the aldehyde moiety is introduced at the N-terminus, and can be generated by oxidative cleavage at adjacent hydroxyl and amino groups found in N-terminal serine or threonine residues.

In another embodiment of the invention, a modified molecule is provided having an increased serum half-life relative to the molecule per se, i.e., the "unmodified" molecule. Preferably, the modified molecule is a polypeptide conjugated to polyethylene glycol through a hydrazone or semicarbazone linkage. In a particularly preferred embodiment, the polypeptide is human urokinase or a fragment thereof, e.g., $uPA_{1-48}$.

In another embodiment of the invention, a method is provided for producing a conjugate of the uPA epidermal growth factor-("EGF-") like domain, particularly $uPA_{1-48}$.

In still another embodiment of the invention, a conjugate of $uPA_{1-48}$ is provided which is useful for inhibiting the mitogenic activity of uPA in cancer cells.

In another embodiment of the invention, a method is provided for treating a uPA-mediated or uPA receptor-mediated disorder by administering a conjugate of $uPA_{1-48}$ and a polymer to a patient in need thereof.

In yet another embodiment of the invention, a method is provided for treating cancer and metastasis by administering an effective amount of a conjugated uPA EGF-like domain, particularly $uPA_{1-48}$.

DETAILED DESCRIPTION OF THE INVENTION

Overview and Definitions:

Before describing the present invention in detail, it is to be understood that this invention is not limited to specific compositions, components or process steps, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a molecule" includes a plurality of molecules and/or a mixture of different molecules, reference to a "polypeptide conjugate" includes a plurality of polypeptide conjugates and/or a mixture of different such conjugates, and the like.

In describing and claiming the present invention, the following terminology will be used in accordance with the definitions set out below.

The terms "uPA" and "huPA" refer specifically to human urokinase-type plasminogen activator. Urokinase plasminogen activator ("uPA") is a multidomain protein which binds to a cell surface receptor and cleaves plasminogen to plasmin. uPA is involved in clot resolution, wound healing, inflammation, tissue restructuring and cancer. Variants of uPA such as $uPA_{1-48}$ have previously been found useful for treating inappropriate angiogenesis, inflammatory disorders and cancer. $uPA_{1-48}$ is a catalytically inactive protein comprising the first 48 amino acids of uPA, and still retains the binding domain for the uPA receptor. $uPA_{1-48}$ thus acts by competing with native uPA for its receptor, and thus inhibiting plasminogen activation. Prior to this invention, nothing was known of the serum half-life of $uPA_{1-48}$, and consequently there was no reason to modify $uPA_{1-48}$ to increase its serum half-life.

The term "$uPA_{1-48}$" refers to a polypeptide having a sequence identical to the EGF-like domain of uPA (residues 1-48), or an active portion thereof. An "active portion" is one which lacks up to 10 amino acids, from either the N-terminal or C-terminal ends, or from both ends, of the $uPA_{1-48}$ polypeptide, and exhibits a Kd less than or equal to about 5 nM with uPAR. The term "active analog" refers to a polypeptide differing from the sequence of the EGF-like domain of $uPA_{1-48}$ or an active portion thereof by 1-7 amino acids, but which still exhibits a Kd less than or equal to about 5 nM with uPAR. The differences are preferably conservative amino acid substitutions, in which an amino acid is replaced with another naturally occurring amino acid of similar character. For example, the following substitutions are considered "conservative": Gly-Ala; Val-Ile-Leu; Asp-Glu; Lys-Arg; Asn-Gln; and Phe-Trp-Tyr. Nonconservative changes are generally substitutions of one of the above amino acids with an amino acid from a different group (e.g., substituting Asn for Glu), or substituting Cys, Met, His, or Pro for any of the above amino acids. The $uPA_{1-48}$ polypeptides should be substantially free of peptides derived from other portions of the uPA protein. For example, a $uPA_{1-48}$ composition should contain less than about 20 wt % uPA B domain ("uPA-B", dry weight, absent excipients), preferably less than about 10 wt % uPA-B, more preferably less than about 5 wt % uPA-B, most preferably no amount detectable by conventional methods well known in the art. The $uPA_{1-48}$ polypeptides also preferably exclude the kringle region of uPA.

The "EGF-like domain" of uPA is that portion of the uPA molecule responsible for mediating uPA binding to its receptor ("uPAR"). The EGF-like domain, sometimes called the growth factor-like domain ("GFD"), is located within the first 48 amino acid residues of uPA. The residues essential for receptor binding activity have been localized to positions 12–32, although a peptide containing only those residues does not exhibit a binding affinity high enough to serve as a useful receptor antagonist.

The terms "uPA-disorder" and "uPA receptor-disorder" refer to a disease state or malady which is caused or exacerbated by a biological activity of uPA. The primary biological activity exhibited is plasminogen activation; other activities are related to cell migration and invasiveness. Disorders by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated uPA is also mitogenic for some tumor cells (e.g., SaOS-2 osteosarcoma cells), which sometimes self-activate in an autocrine mechanism. Accordingly, $uPA_{1-48}$ is effective in inhibiting the proliferation of uPA-activated tumor cells.

The term "effective amount" refers to an amount of a biologically active molecule or conjugate thereof sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The effective amount for a subject will depend upon the subject's size and health, the nature and severity of the condition to be treated, and the like. Thus, it is not possible to specify an exact effective amount in advance. However, the effective amount for a given situation can be determined by one of skill in the art using routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like, and the salts of organic acids such as acetates, propionates, malonates, benzoates, and the like.

By "polypeptide" is meant a molecule comprising a series of amino acids linked through amide linkages along the alpha carbon backbone. Modifications of the peptide side chains may be present, along with glycosylations, hydroxylations and the like. Additionally, other nonpeptide molecules, including lipids and small molecule agents, may be attached to the polypeptide.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

By "biologically active" is meant the ability to modify the physiological system of an organism. A molecule can be biologically active through its own functionalities, or may be biologically active based on its ability to activate or inhibit molecules having their own biological activity. "Biologically active molecules" include, but are not limited to, small organic compounds, nucleic acids and nucleic acid derivatives, saccharides or oligosaccharides, peptide mimetics including peptides, proteins, and derivatives thereof, such as peptides containing non-peptide organic moieties, synthetic peptides which may or may not contain amino acids and/or peptide bonds, but retain the structural and functional features of a peptide ligand, and peptoids and oligopeptoids which are molecules comprising N-substituted glycine, such as those described by Simon et al., *Proc. Natl. Acad. Sci. USA* 89:9367 (1992), and antibodies, including anti-idiotype antibodies.

A "peptoid" is a polymer made up, at least in part, of monomer units of "amino acid substitutes", which are any molecule other than an amino acid, but which serve in the peptoid polymer to mimic an amino acid. Particularly preferred monomer units are N-alkylated derivatives of glycine. Peptoids are produced by linking the "amino acid substitutes" into a linear chain or cyclic structure with amino acids and/or other amino acid substitutes. The links may include, peptide bonds, esters, ethers, amines, phosphates, sulfates, sulfites, thioethers, thioesters, aliphatic bonds, carbamates and the like. Examples of amino acid substitutes include N-substituted glycine, N-alkylated glycines, N-substituted alanine, N-substituted D-alanine, urethanes, substituted hydroxy acids, such as hydroxyacetic acid, 2-hydroxypropanoic acid, 3-hydroxypropanoic acid, 3-phenyl-2-hydroxypropanoic acid, and the like. A peptoid may comprise amino acid substitutes using more than one type of link provided the chemistry for the reaction schemes are compatible and encompassed generally by the reactions described herein. Other examples of amino acid substitutes and peptoids are described in Bartlett et al., PCT WO91/19735 and Zuckermann et al., PCT WO94/06451.

The terms "conventional" and "naturally occurring" as applied to peptides herein refer to polypeptides, also referred to as proteins, constructed only from the naturally occurring amino acids: Ala, Cys, Asp, Glu, Phe, Gly, His, Ile, Lys, Leu, Met, Asn, Pro, Gln, Arg, Ser, Thr, Val, Trp and Tyr.

By "conjugated" is meant the covalent linkage of at least two molecules. As described herein, a biologically active molecule is conjugated to a pharmaceutically acceptable polymer to increase its serum half-life. The polymer may or may not have its own biological activity. The suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. In a preferred embodiment, the polymer is PEG.

By "PEGylated" is meant the covalent attachment of at least one molecule of polyethylene glycol to a biologically active molecule. The average molecular weight of the reactant PEG is preferably between about 5,000 and about 50,000 daltons, more preferably between about 10,000 and about 40,000 daltons, and most preferably between about 15,000 and about 30,000 daltons. Particularly preferred are PEGs having nominal average sizes of about 20,000 and about 25,000 daltons. The method of attachment is not critical, but preferably does not alter, or only minimally alters, the activity of the biologically active molecule. Preferably the increase in half-life is greater than any decrease in biological activity. A preferred method of attachment is via N-terminal linkage to a polypeptide. PEGylated uPA$_{1-48}$ is sometimes referred to herein as PEG hu1-48.

By "increase in serum half-life" is meant the positive change in circulating half-life of a modified biologically active molecule relative to its non-modified form. Serum half-life is measured by taking blood samples at various time points after administration of the biologically active molecule, and determining the concentration of that molecule in each sample. Correlation of the serum concentration with time allows calculation of the serum half-life. The increase is desirably at least about two-fold, but a smaller increase may be useful, for example where it enables a satisfactory dosing regimen or avoids a toxic effect. Preferably the increase is at least about three-fold, more preferably at least about five-fold, and most preferably at least about ten-fold, and most preferably at least about fifteen-fold. Increases of up to 28.8-fold in serum half-life are demonstrated herein.

The increase in serum half-life preferably occurs through a method that at least preserves biological activity, measured, for example, in a binding assay. In some instances, the method may even increase biological activity. However, where the method does provide a decrease in biological activity, it is preferable that the proportionate increase in serum half-life is at least as great as the proportionate decrease in biological activity. More preferably, the increase in serum half-life is greater than the decrease in biological activity, proportionately. This is not an absolute requirement, and depends, for example, on the pharmacokinetics and toxicity of the specific derivative. The percentage of biological activity which is retained is preferably about 10 to about 100%, more preferably about 15 to about 100%, and most preferably about 20 to about 100%. In an especially preferred embodiment, about 25 to about 100% of the biological activity is retained.

In a preferred embodiment, the biologically active molecule is a polypeptide. A particularly preferred polypeptide is $uPA_{1-48}$. $uPA_{1-48}$ is herein demonstrated to have a short serum half-life. Increasing the serum half-life of rapidly cleared compounds is desirable, particularly where the compounds are recombinant molecules which are difficult and costly to produce. Such an increase in half-life can reduce treatment costs, decrease the amount of agent administered, decrease the duration of administration, and lessen the exposure of patients to large volumes of pharmaceutical preparations. Conjugation of PEG to $uPA_{1-48}$ is shown herein to dramatically increase its serum half-life by as much as 28.8 fold.

The polypeptide can be produced by any suitable means, such as expression in a recombinant host cell or by chemical synthesis. The polypeptide is then purified through standard methods. Where the polypeptide is $uPA_{1-48}$, production in a yeast host cell, as described in published PCT patent application WO 94/28145, is suitable. For example, DNA encoding residues 1-48 of mature human uPA are cloned into a yeast expression vector as a fusion with the yeast alpha-factor leader ($\alpha$F1), under transcriptional control of a hybrid ADH2-GAP promoter. The PCR fragment of the gene encoding huPA primer and a template plasmid, and the alkaline phosphatase treated pCBR subcloning vector containing the yeast expression cassette are digested with BgIII, followed by ligation. The subclone thus obtained (pCBRuPA$\alpha$13) is subjected to BamHI digestion and the isolated expression cassette is ligated into the yeast shuttle vector. The expression plasmid is then transformed into the yeast host under conditions to promote the expression of the polypeptide. $uPA_{1-48}$ can then be purified as described therein, or by suitable techniques known in the art, such as centrifugation, column chromatography, anion exchange chromatography, cation exchange chromatography, or combinations thereof. Diafiltration can be used to bring the polypeptide solution to a desired concentration and/or to change the composition of the solution.

The biologically active molecule can be linked to a polymer through any available functionality using standard methods well known in the art. It is preferred that the biologically active molecule be linked at only one position in order to minimize any disruption of its activity and to produce a pharmacologically uniform product. Nonlimiting examples of functional groups on either the polymer or biologically active molecule which can be used to form such linkages include amine and carboxy groups, thiol groups such as in cysteine resides, aldehydes and ketones, and hydroxy groups as can be found in serine, threonine, tyrosine, hydroxyproline and hydroxylysine residues.

The polymer can be activated by coupling a reactive group such as trichloro-s-triazine (Abuchowski et al., (1977), *J. Biol. Chem.* 252:3582–3586), carbonylimidazole (Beauchamp et al., (1983), *Anal. Biochem.* 131:25–33), or succinimidyl succinate (Abuchowski et al., (1984), *Cancer Biochem. Biophys.* 7:175–186) in order to react with an amine functionality on the biologically active molecule. Another coupling method involves formation of a glyoxylyl group on one molecule and an aminooxy, hydrazide or semicarbazide group on the other molecule to be conjugated (Fields and Dixon, (1968), *Biochem. J.* 108:883–887; Gaertner et al., (1992), *Bioconjugate Chem.* 3:262–268; Geoghegan and Stroh, (1992), *Bioconjugate Chem.* 3:138–146; Gaertner et al., (1994), *J. Biol. Chem.* 269:7224–7230). Other methods involve formation of an active ester at a free alcohol group of the first molecule to be conjugated using chloroformate or disuccinimidylcarbonate, which can then be conjugated to an amine group on the other molecule to be coupled (Veronese et al., (1985), *Biochem. and Biotech.* 11:141–152; Nitecki et al., U.S. Pat. No. 5,089,261; Nitecki, U.S. Pat. No. 5,281,698). Other reactive groups which may be attached via free alcohol groups are set forth in Wright, published European patent application 0 539 167 A2, which also describes the use of imidates for coupling via free amine groups.

An aldehyde functionality useful for conjugating the biologically active molecule can be generated from a functionality having adjacent amino and alcohol groups. Where the biologically active molecule is a polypeptide, for example, an N-terminal serine, threonine or hydroxylysine can be used to generate an aldehyde functionality via oxidative cleavage under mild conditions using periodate. These residues, or their equivalents, can be normally present, for example at the N-terminus of a polypeptide, may be exposed via chemical or enzymatic digestion, or may be introduced via recombinant or chemical methods. The reaction conditions for generating the aldehyde typically involve addition of a molar excess of sodium meta periodate and under mild conditions to avoid oxidation at other positions in the protein. The pH is preferably about 7.0. A typical reaction involves the addition of a 1.5 fold molar excess of sodium meta periodate, followed by incubation for 10 minutes at room temperature in the dark.

The aldehyde functionality can then be coupled to an activated polymer containing a hydrazide or semicarbazide functionality to form a hydrazone or semicarbazone linkage. Hydrazide-containing polymers are commercially available, and can be synthesized, if necessary, using standard techniques. PEG hydrazides preferred for the invention can be obtained from Shearwater Polymers, Inc., 2307 Spring Branch Road, Huntsville, Ala. 35801. The aldehyde is then coupled to the polymer by mixing the solution of the two components together and heating to about 37° C. until the reaction is substantially complete. An excess of the polymer hydrazide is typically used to increase the amount of conjugate obtained. A typical reaction time is 26 hours. Depending on the thermal stability of the reactants, the reaction temperature and time can be altered to provide suitable results. Detailed determination of reaction conditions for both oxidation and coupling is set forth in Geoghegan and Stroh, (1992), *Bioconjugate Chem.* 3:138–146, and in Geoghegan, U.S. Pat. No.

Such a conjugate formed between $uPA_{1-48}$ and a polymer can be used therapeutically to treat uPA- and uPA receptor-mediated disorders. A pharmaceutically acceptable solution containing the conjugate is prepared, and a therapeutically effective dose of the conjugate is administered to an individual having a uPA-mediated or a uPA receptor-mediated disorder. The conjugate is preferably administered via injection either intravenously or, more preferably, subcutaneously. Administration is repeated as necessary in order to maintain therapeutically effective levels of the conjugate.

Pharmaceutical compositions comprising a conjugate of a biologically active molecule and a polymer can be prepared by mixing the conjugate with any pharmaceutically acceptable component, such as, for example, a carrier, a medicinal agent, an adjuvant, a diluent, and the like, as well as combinations of any two or more thereof. Suitable pharmaceutical carriers, medicinal agents, adjuvants, and diluents are described in "Remington's Pharmaceutical Sciences," 18th edition, by E. W. Martin (Mack Publ. Co., Easton, Pa.).

The composition may be administered in a variety of ways, including, for example, orally, parenterally (e.g., intravenously), by intramuscular injection, by intraperitoneal injection, as suppositories, etc. The specific amount of active conjugate administered will, of course, depend on the subject being treated, the subject's weight, the manner of administration and the judgment of the prescribing physician. Information concerning dosages of various pharmacological agents may be found in standard pharmaceutical reference books, e.g., "Remington's Pharmaceutical Sciences," supra. The pharmaceutical compositions may be in solid, semi-solid or liquid dosage forms, such as, for example, tablets, pills, capsules, powders liquids, suspensions, and the like.

It is to be understood that while the invention has been described in conjunction with the preferred specific embodiments thereof, the foregoing description as well as the examples which follow are intended to illustrate and not limit the scope of the invention. Other aspects, advantages and modifications within the scope of the invention will be apparent to those skilled in the art to which the invention pertains.

All patents, patent applications, journal articles and other publications cited herein are incorporated by reference in their entireties.

EXAMPLE 1

Determination of the Half-Life of $uPA_{1-48}$ $uPA_{1-48}$ was produced in yeast, purified and concentrated into PBS. When produced in yeast, $uPA_{1-48}$ lacks a fucosylation which is present when the protein is expressed in mammalian cells. The purified protein was injected intravenously into mice. Blood samples were collected at various time points, and the amount of $uPA_{1-48}$ present in each sample was determined. The serum half-life of $uPA_{1-48}$ was found to be approximately 10 minutes in mice.

EXAMPLE 2

Generation of a Polypeptide with an N-Terminal Aldehyde

A half liter solution of $uPA_{1-48}$ at 10-13 mg/ml in 50 mM sodium phosphate, pH 6.8, was prepared. The molar concentration of the solution was determined via spectrometric methods. A 1.5 molar excess of freshly prepared sodium meta periodate (MW=214 μg/μmole) was added and mixed, and the resulting solution was incubated in the dark for 10 minutes at room temperature. The product were separated from excess periodate and isolated using tangential diafiltration with 30 mM sodium acetate, pH 4.5.

EXAMPLE 3

Coupling of PEG Hydrazide to $uPA_{1-48}$ Aldehyde

PEG hydrazides were obtained commercially (Shearwater Polymers, Inc., 2307 Spring Branch Road, Huntsville, Ala. 35801). PEG hydrazides having nominal average molecular weights of 3.4 kD, 5 kD, 20 kD and 25 kD, and having a single hydrazide group at one end of the polymer, were used. Additionally, a PEG hydrazide of average molecular weight of 50 kD, having a hydrazide group at each end of the polymer so that two $uPA_{1-48}$ molecules could be conjugated, was used. The concentration of the N-terminal aldehyde solution was determined, and a two fold molar excess of each PEG hydrazide was added, in separate reactions, to the $uPA_{1-48}$ N-terminal aldehyde produced in Example 2. The reaction mixtures were incubated for 26 hrs. at 37° C. Approximately 60% of the $uPA_{1-48}$ molecules were conjugated to PEG following the reactions. The conjugates were purified via column chromatography. The conjugates were then diafiltered and concentrated into PBS to approximately 8–10 mg/ml. The products were then frozen at –70° C. until use.

EXAMPLE 4

Determination of the Half-Life of the PEG Conjugates

Pharmaceutical preparations comprising the conjugates of $uPA_{1-48}$ and PEG were injected intravenously into mice. Blood samples were collected at various time points, and the amount of conjugate present in the blood was determined for each time point. The half-life of the $uPA_{1-48}/PEG_{25\,kD}$ conjugate was found to be 277 minutes. The half-life of the $uPA_{1-48}/PEG_{50\,kD}$ dimeric conjugate (i.e., having a $uPA_{1-48}$ molecule conjugated at each end of $PEG_{50\,kD}$ as described in Example 3) was found to be 288 minutes. The half-life of the $uPA_{1-48}/PEG_{20\,kD}$ conjugate was found to be 130 minutes. The half-life of the $uPA_{1-48}/PEG_{5\,kD}$ conjugate was found to be 44 minutes. The half-life of the $uPA_{1-48}/PEG_{3.4\,kD}$ conjugate was found to be 12 minutes.

Pharmaceutical preparations comprising the conjugates of $uPA_{1-48}$ and PEG (20 kD) at a dose of 10 mg/kg were injected as a single IV bolus or via subcutaneous administration into cynomologous monkeys. As above, blood samples were collected at various time points, and the amount of conjugate present in the blood was determined for each time point. The method measures the receptor binding activity instead of just the total protein present; thus the amount of protein measured as a function of time represents the active protein, and the measured half-life represents functional half-life. The data is shown in Table 1, and a graph illustrating plasma disposition of PEG hu1-48 over time is included in FIG. 1.

TABLE 1

Pharmacokinetic Parameters of PEG hu1-48 after Single IV bolus or SC dose at 10 mg/kg Determined by the Non-Compartment Model

| Monkey: | F67-344F | | F7238F | | F7281F | |
|---|---|---|---|---|---|---|
| Route: | IV | SC | IV | SC | IV | SC |
| Dose (mg/kg) | 10 | 10 | 10 | 10 | 8.8 | 10 |
| AUC (min*nM) | 3297918 | 3803604 | 3002085 | 3057502 | 1987996 | 2337888 |

TABLE 1-continued

Pharmacokinetic Parameters of PEG hu1-48 after Single IV bolus
or SC dose at 10 mg/kg Determined by the Non-Compartment Model

| Monkey: | F67-344F | | F7238F | | F7281F | |
|---|---|---|---|---|---|---|
| Route: | IV | SC | IV | SC | IV | SC |
| CL (mL/min/kg) | 0.6 | NA | 0.6 | NA | 0.8 | NA |
| $C_{max}$ (nM) | 19143 | 2596 | 30564 | 2155 | 19199 | 1126 |
| $T_{max}$ (hr) | 0 | 8 | 0 | 4 | 0 | 8 |
| Vss (L/kg) | 0.252 | NA | 0.249 | NA | 0.255 | NA |
| $t_{1/2}$ (hr.) | 6.9 | 23 | 7.6 | 26 | 6.4 | 14 |
| MRT (hr) | 7.4 | 31 | 6.6 | 28 | 5.1 | 31 |
| F (%) | 100 | 115 | 100 | 101 | 100 | 103 |

EXAMPLE 5

Comparison of the Activity of uPA$_{1-48}$ and its PEG Conjugates

The uPAR receptor binding activity of uPA$_{1-48}$ and the PEG conjugates thereof were determined by the method of Goodson et al. (1994) *PNAS* 91:7129–7133. uPA$_{1-48}$ was found to have an IC$_{50}$ of 250 pM. The PEG$_{20\ kD}$ conjugate was found to have an IC$_{50}$ of 1 nM. The PEG$_{20\ kD}$ conjugate therefore exhibited a 13-fold increase in serum half-life, with only a four-fold decrease in biological activity.

EXAMPLE 6

Effect on Breast Cancer Carcinoma

Thirty NOD/Ltz mice were injected subcutaneously with 2×10$^6$ MDA MB231 cells (human breast carcinoma) on day 0. The mice were divided into three groups of 10 mice each, and the treatment of the three groups of mice began on day 1. Twice every week, group 1 was subcutaneously injected with 30 μg PEG hu1-48 (20 kD PEG), group 2 was subcutaneously injected with 300 μg PEG hu1-48 (20 kD PEG), and group 3 was subcutaneously injected with the vehicle (PBS). Treatment was continued for 9 weeks. The primary tumor volume (mm$^3$) was measured three times per week for 12 weeks, and the experiment was terminated when mean tumor volume in vehicle control group exceeded 2000 mm$^3$. The data, illustrated in FIG. 2, shows that the tumor growth was reduced 77% in the treatment group receiving 30 μg PEG hu1-48, and 98% in the group receiving 300 μg PEG hu1-48, when compared to the group receiving the vehicle control at 9 weeks (p=0.05). The 300 μg treatment group was observed for an additional 3 weeks after treatment was stopped (day 63). Tumors become evident in this group by day 84, indicating that administration of PEG hu1-48 had a cytostatic effect.

EXAMPLE 7

Effect on Human Prostate Carcinoma

The prostates of 18 nude mice were injected with 1×10$^5$ PC-3 mm2 cells (human prostate carcinoma) on day 0. The mice were divided into two groups of nine mice each, and treatment was initiated on day 3 and continued for 3 weeks. Twice per week, the mice of group 1 received 300 μg PEG hu1-48 (20 kD PEG) by subcutaneous administration, and the mice of group 2 received vehicle only by subcutaneous administration. Three weeks after the implantation of the human prostate carcinoma cells, the prostates of the mice were excised and weighed to determine effects of treatment on the primary tumor growth. The data, collected in FIG. 3, showed about a 57% reduction in primary tumor growth in mice treated with PEG hu1-48 when compared with the mice in the control group. Thus, the data indicates that PEG hu1-48 significantly reduces primary tumor.

EXAMPLE 8

Effect on Colon Cancer Tumor Growth and Liver Metastases

Twenty 10 week old Nude male mice were injected intrasplenically with 1×10$^6$ KM12 L4A cells (human colorectal adenocarcinoma) on day 0. The mice were divided into two groups, and treatment was initiated on day 1 post-implantation and continued for 4 weeks. Group 1, consisting of 10 mice, were subcutaneously injected five times per week with PEG hu1-48 (20 kD PEG) and 250 μg BID while group 2 mice acted as the control and were injected with vehicle only. The animals were sacrificed all 5 weeks, and the spleens of the animals from each group were weighed to determine primary tumor burden (FIG. 4A). The livers were weighed to determine metastatic tumor burden, and were scored by histological examination for incidence of metastases (FIG. 4B). All 10 animals in the control group that were treated with vehicle only had visible primary tumors in the spleen, and had an average spleen weight of 641 mg±307 while only 7 mice treated with PEG hu1-48 had visible tumors in the spleen, with an average spleen weight of 269 mg±113.(FIG. 4A). For the purposes of comparison, the average splenic weight for mice in this age group is about 240 mg. In addition, 6 mice in the control group had incidence of liver metastases, compared to no observed metastases in the livers of the group treated with PEG hu1-48 (FIG. 4B). The differences between the two groups of mice for both primary tumor burden and incidence of metastases is statistically significant (p<0.005), and is indicates that PEG hu1-48 has efficacy in reducing tumor growth and metastasis.

EXAMPLE 9

Effect on Incidence of Liver Metastases in Post-Resection Colorectal Carcinoma Model Thirty male Nu/Nu mice were injected intrasplenically with 0.5×10$^6$ KM12 L4A cells (human colorectal carcinoma cancer with high metastatic potential), and the spleens of all the mice were removed 3 days after implantation of the KM12 L4A cells. The mice were divided into two treatment groups, and treatment was began 6 days after implantation.

Figures 5A, 5B:
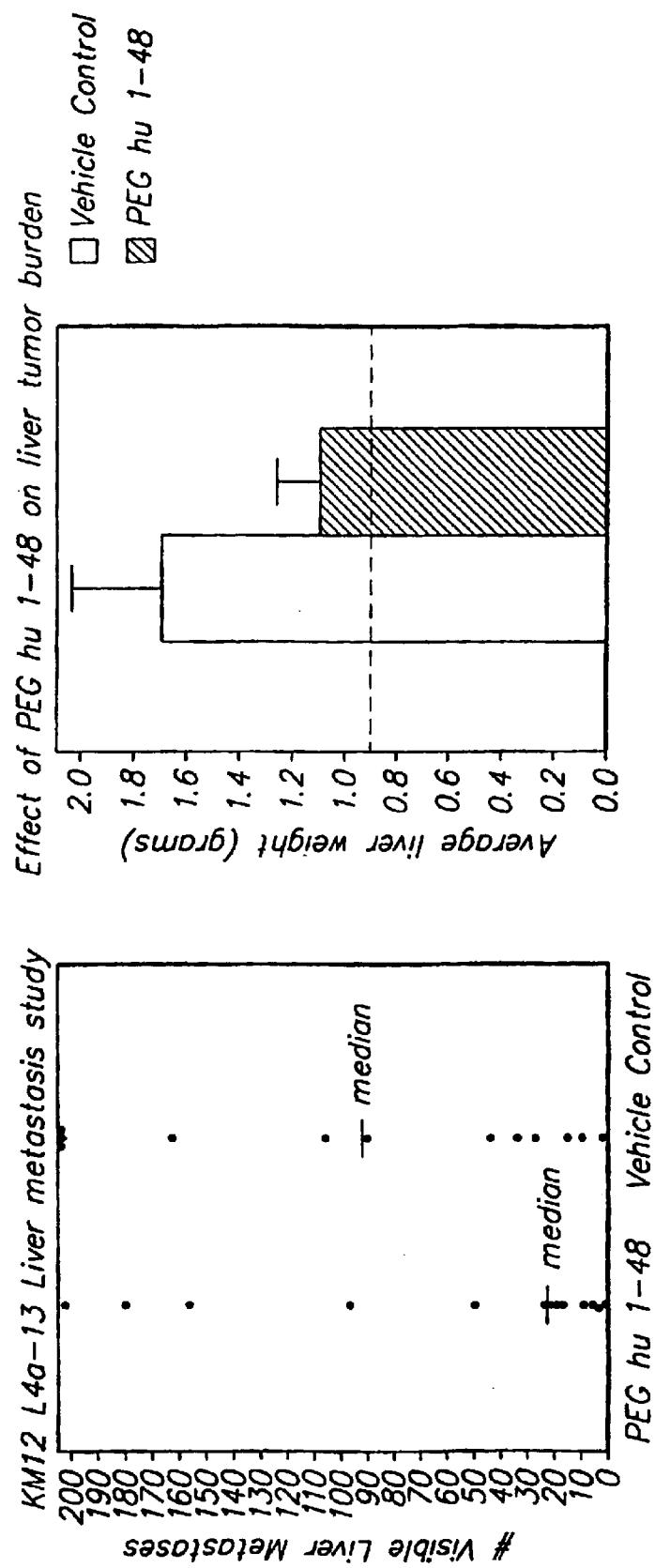
FIG. 5A is a graph illustrating the number of visible liver metastases to the liver of nude mice injected intrasplenically with human colorectal carcinoma cancer KM12 L4A cells followed by treatment with PEG hu1-48, as evaluated in Example 9.
FIG. 5B illustrates the effect of PEG hu1-48 on liver tumor burden, also as evaluated in Example 9.

The first group of 15 mice received subcutaneous administrations of 1000 μg PEG hu1-48(20 kD PEG) twice per week, and the second group of 15 mice received saline vehicle only and served as the control group. The experiment was terminated 27 days after implantation of the KM12 L4A cells, and the weight of the livers were determined and histologically scored for metastatic foci. The mice of the first group that had been treated with PEG hu1-48 showed significantly reduced metastases to the liver (p value <0.05) when compared to the mice in the control group that received vehicle only (FIG. 5A), even when treatment was initiated 5 days after tumor implantation. A trend toward a reduction in overall liver tumor burden was observed as well (FIG. 5B).

EXAMPLE 10

Treatment of a uPA-Mediated Disorder in Humans

A pharmaceutically acceptable solution comprising the $PEG_{20\ kD}$ conjugate of $uPA_{1-48}$ at 5–10 mg/ml in a pharmaceutically acceptable carrier is administered subcutaneously at a dose of 1–10 mg/kg to a human patient having a uPA-mediated disorder. Administration is repeated at intervals sufficient to maintain therapeutically effective serum levels of the conjugate in the patient.

What is claimed is:

1. A method for preparing a biologically active polypeptide having an increased serum half-life, comprising coupling the polypeptide to a polymer by reacting an aldehyde functionality on the polypeptide with a hydrazide or semicarbazide group on the polymer under reaction conditions effective to promote formation of a conjugated polypeptide, wherein the polypeptide is bound to the polymer through a hydrazone or semicarbazone linkage.

2. The method of claim 1 wherein the polypeptide has molecular weight of less than 50,000 daltons.

3. The method of claim 2, wherein the polypeptide as a molecular weight of less than 30,000 daltons.

4. The method of claim 3, wherein the polypeptide as a molecular weight of less than 10,000 daltons.

5. The method of claim 4, wherein the polypeptide is urokinase-type plasminogen activator$_{1-48}$ (uPA$_{1-48}$) or an active portion thereof, wherein the active portion is a portion of uPA$_{1-48}$ that lacks up to 10 amino acids, from either the N-terminal or C-terminal ends, or from both ends, and exhibits a Kd less than or equal to about 5 nM with the uPA receptor.

6. A modified polypeptide comprising a biologically active polypeptide conjugated to a polymer having a hydrazide or semicarbazide group, wherein said modified polypeptide exhibits a proportional increase in serum half-life compared to the unmodified polypeptide which is greater than any proportional decrease in its biological activity compared to the unmodified polypeptide.

7. The modified polypeptide of claim 6, wherein the increase in half-life is at least about three fold.

8. The modified polypeptide of claim 6, wherein th biologically active polypeptide is a urokinase.

9. The modified polypeptide of claim 8, wherein the urokinase is urokinase-type plasminogen activator$_{1-48}$ (uPA$_{1-48}$) or an active portion thereof, wherein the active portion is a portion of uPA$_{1-48}$ that lacks up to 10 amino acids, from either the N-terminal or C-terminal ends, or from both ends, and exhibits a Kd less than or equal to about t 5 nM with the urokinase-type plasminogen activator receptor.

10. The modified polypeptide of claim 9, wherein the polymer is linked at the N-terminus of uPA$_{1-48}$.

11. A pharmaceutical composition comprising a therapeutically effective amount of the modified polypeptide of claim 9, in combination with a pharmaceutically acceptable carrier or excipient.

12. The modified polypeptide of claim 9, wherein the polymer is polyethylene glycol.

13. A pharmaceutical composition comprising a therapeutically effective amount of the modified polypeptide of claim 12, in combination with pharmaceutically acceptable carrier or excipient.

14. The modified polypeptide of claim 12, wherein the polyethylene glycol has an average molecular weight of about 5,000 to about 50,000 daltons.

15. The modified polypeptide of claim 14, wherein the polyethylene glycol has an average molecular weight of about 10,000 to about 40,000 daltons.

16. The modified polypeptide of claim 15, wherein the polyethylene glycol has an average molecular weight of about 15,000 to about 30,000 daltons.

* * * * *